(12) United States Patent
Kizaki et al.

(10) Patent No.: US 7,794,993 B2
(45) Date of Patent: Sep. 14, 2010

(54) CARBONYL REDUCTASE, GENE THEREOF AND METHOD OF USING THE SAME

(75) Inventors: Noriyuki Kizaki, Takasago (JP); Miho Yano, Takasago (JP); Masahiro Funaki, Takasago (JP); Teruaki Takesue, Takasago (JP); Yoshihiko Yasohara, Takasago (JP); Souichi Morikawa, Takasago (JP); Takahisa Nakai, Takasago (JP); Michihiko Kataoka, Kyoto (JP); Sakayu Shimizu, Kyoto (JP)

(73) Assignee: Kaneka Corporation, Osaka (JP)

( * ) Notice: Subject to any disclaimer, the term of this patent is extended or adjusted under 35 U.S.C. 154(b) by 536 days.

(21) Appl. No.: 11/659,481

(22) PCT Filed: Aug. 1, 2005

(86) PCT No.: PCT/JP2005/014006

§ 371 (c)(1),
(2), (4) Date: Feb. 6, 2007

(87) PCT Pub. No.: WO2006/013801

PCT Pub. Date: Feb. 9, 2006

(65) Prior Publication Data
US 2008/0261281 A1 Oct. 23, 2008

(30) Foreign Application Priority Data
Aug. 6, 2004 (JP) ............................. 2004-231226

(51) Int. Cl.
*C07H 21/00* (2006.01)
*C12N 15/00* (2006.01)
*C12N 5/10* (2006.01)
*C12N 1/21* (2006.01)
*C12P 7/16* (2006.01)
*C12P 21/00* (2006.01)
*C12N 9/02* (2006.01)
*C07K 14/00* (2006.01)

(52) U.S. Cl. .................... 435/189; 435/320.1; 435/325; 435/252.3; 435/69.1; 435/252.33; 435/155; 435/160; 530/350; 536/23.2

(58) Field of Classification Search .................. 435/189, 435/320.1, 325, 252.3, 69.1, 252.33, 25; 530/350; 536/23.2
See application file for complete search history.

(56) References Cited

U.S. PATENT DOCUMENTS 7,335,757 B2 * 2/2008 Hiraoka et al. ............. 536/23.2
2005/0048633 A1 3/2005 Hiraoka et al.

FOREIGN PATENT DOCUMENTS

| EP | 1 491 633 A1 | 12/2004 |
|---|---|---|
| JP | 2003-339387 | 12/2003 |
| JP | 2004-254554 A | 9/2004 |
| WO | WO 03/007863 A1 | 1/2003 |
| WO | WO 03/078634 A1 | 9/2003 |

OTHER PUBLICATIONS

Atalla et al., Chemico-Biological Interactions 130-132:737-748, 2001.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Phillips, A., J. Pharm. Pharmacology 53:1169-1174, 2001.*
Gardlik et al., Med. Sci. Monit. 11(4):RA110-121, 2005.*
Houdebine, L., Journal of Biotechnology 98:145-160, 2002.*
Kappel et al., Current Opinion in Biotechnology 3:548-553, 1992.*
Mullins et al., Hypertension 22(4):630-633, 1993.*
Ausubel, F., Current Protocols in Molecular Biology, Hybridization Analysis of DNA Blots, pp. 2.10.8-2.10.11.*
M. Kataoka et al, "Novel bioreduction system for the production of chiral alcohols", Applied Microboiology and Biotechnology, Springer Verlag, Berlin, DE, vol. 62, No. 5-6, Oct. 2003, pp. 437-445, XP009049508.

* cited by examiner

*Primary Examiner*—Delia M Ramirez
(74) *Attorney, Agent, or Firm*—Sughrue Mion, PLLC (57) ABSTRACT

The present invention relates to a polypeptide having an activity to asymmetrically reduce (3S)-1-chloro-3-tert-butoxycarbonylamino-4-phenyl-2-butanone to produce (2R,3S)-1-chloro-3-tert-butoxycarbonylamino-4-phenyl-2-butanol isolated from a microorganism belonging to the genus *Ogataea*, a DNA encoding the polypeptide and a transformant that produces the polypeptide. The present invention moreover relates to a method of producing (2R,3S)-1-chloro-3-tert-butoxycarbonylamino-4-phenyl-2-butanol utilizing the polypeptide or the transformant. Using the polypeptide or transformant of the present invention, optically active alcohols such as (2R,3S)-1-chloro-3-tert-butoxycarbonylamino-4-phenyl-2-butanol and the like can be produced efficiently.

15 Claims, 1 Drawing Sheet

FIG. 1

SEQUENCE LISTING

<160> NUMBER OF SEQ ID NOS: 16

<210> SEQ ID NO 1
<211> LENGTH: 756
<212> TYPE: DNA
<213> ORGANISM: Ogataea minuta var. minuta

<400> SEQUENCE: 1

```
atggctaaga ctgtctattt cattgccgga gcatcgagag ggattggcct cgagattgca      60
acccaattga gtgcaaaccc agagaaccat gtgattgcct cgtacagatc tgaaaagact     120
gctggtgcac tcctggaact tgccaagaag acaacgtgg acactgttgt gttggatatt     180
gcaatccagg agtcgattga gggtttgtcc aacagattg tgaagctgac ggacggaatt     240
gatattgctc tgatcaatgc cggagttgga tactcaatgt actctctact cgaatgttcc     300
agagaagcat tcattgacca ctggactaca aattctctgg gtccaatcct ggtgtataag     360
gaaatccacc aattcatgct gaagagagaa actcgaaaag tgttcttcat gtctagcgga     420
gcagggtcta ttcagggcca cttgcctgtt tccgtgagtg catacggtat gtcgaaggca     480
gcactgaact acgcggcccg gaaactttct gacgaatgct acaaagacgg ctttactatt     540
gtggcgcttc acccaggtat ggttctgaca gacatgggta tggagagtat tgagattatg     600
gcaaacggag acgagcagct tgccgcgtcc atcaacagta ttgcaattag tacagacact     660
agtgccgcac aatgcattgg tgcaatgcag agtcttacaa agcagagcaa cggtagattc     720
attaatgttg cagaccagtt tgacattcca ttctag                               756

<210> SEQ ID NO 2
<211> LENGTH: 756
<212> TYPE: DNA
<213> ORGANISM: Ogataea minuta var. minuta

<400> SEQUENCE: 2
atgaccaaga ctgtttattt cattgccgga gcttctagag gtattggcct tgaggttgcc      60
actcagctga gtgccaaccc agataattat gttattggtt cttacagaac ggagaaaact     120
gcagctgagc tgctcaaaac tggccaacaaa gaaaatgtcg acactgttgt cctagacatt     180
ggtagccaag gttctattga agcgcttcca gcacaaatct caaagctgac ggacggaatc     240
gatattactc tgatcaatgc cggaattgcg tactcaatgt actctatttt cgagtgttcc     300
agagagacat ttattgatca ctggaccaca aattccttgg gtccaatcat gctctacaag     360
gagattcatc agttcatgct gaagagagaa actcgtaagg tgtttttcat gtctagtgga     420
ggaggctcta tccagtctct attgcctatt tcaaccagtg cttacggtat gtcgaaggct     480
gcactgaact atgcggtccg gaagctttct gatgaatgct acaaggacaa cttcaccatt     540
gtgatgttgc acccaggagt ggtggccacg gatatgggcc gggaaactac caagatcatg     600
gccaatggaa atgctcagat tatctcttat attgaatcca tatctttgcc gcccgctaca     660
agcgctgcac agactattgg tgcaatgcaa gctcttgaca gcagagcaa tggtaggttc     720 atcggagtcg cagaccagtt cgacattcca tttttaa                              756

<210> SEQ ID NO 3
<211> LENGTH: 251
<212> TYPE: PRT
<213> ORGANISM: Ogataea minuta var. minuta

<400> SEQUENCE: 3

Met Ala Lys Thr Val Tyr Phe Ile Ala Gly Ala Ser Arg Gly Ile Gly
1               5                   10                  15

Leu Glu Ile Ala Thr Gln Leu Ser Ala Asn Pro Glu Asn His Val Ile
            20                  25                  30

Ala Ser Tyr Arg Ser Glu Lys Thr Ala Gly Ala Leu Leu Glu Leu Ala
        35                  40                  45

Lys Lys Asp Asn Val Asp Thr Val Val Leu Asp Ile Ala Ile Gln Glu
    50                  55                  60
```

-continued

```
Ser Ile Glu Gly Leu Ser Gln Gln Ile Val Lys Leu Thr Asp Gly Ile
 65                  70                  75                  80

Asp Ile Ala Leu Ile Asn Ala Gly Val Gly Tyr Ser Met Tyr Ser Leu
                 85                  90                  95

Leu Glu Cys Ser Arg Glu Ala Phe Ile Asp His Trp Thr Thr Asn Ser
            100                 105                 110

Leu Gly Pro Ile Leu Val Tyr Lys Glu Ile His Gln Phe Met Leu Lys
        115                 120                 125

Arg Glu Thr Arg Lys Val Phe Phe Met Ser Ser Gly Ala Gly Ser Ile
    130                 135                 140

Gln Gly His Leu Pro Val Ser Val Ser Ala Tyr Gly Met Ser Lys Ala
145                 150                 155                 160

Ala Leu Asn Tyr Ala Ala Arg Lys Leu Ser Asp Glu Cys Tyr Lys Asp
                165                 170                 175

Gly Phe Thr Ile Val Ala Leu His Pro Gly Met Val Leu Thr Asp Met
            180                 185                 190

Gly Met Glu Ser Ile Glu Ile Met Ala Asn Gly Asp Glu Gln Leu Ala
        195                 200                 205

Ala Ser Ile Asn Ser Ile Ala Ile Ser Thr Asp Thr Ser Ala Ala Gln
    210                 215                 220

Cys Ile Gly Ala Met Gln Ser Leu Thr Lys Gln Ser Asn Gly Arg Phe
225                 230                 235                 240

Ile Asn Val Ala Asp Gln Phe Asp Ile Pro Phe
                245                 250

<210> SEQ ID NO 4
<211> LENGTH: 251
<212> TYPE: PRT
<213> ORGANISM: Ogataea minuta var. minuta

<400> SEQUENCE: 4

Met Thr Lys Thr Val Tyr Phe Ile Ala Gly Ala Ser Arg Gly Ile Gly
 1               5                  10                  15

Leu Glu Val Ala Thr Gln Leu Ser Ala Asn Pro Asp Asn Tyr Val Ile
                20                  25                  30

Gly Ser Tyr Arg Thr Glu Lys Thr Ala Ala Glu Leu Leu Lys Leu Ala
            35                  40                  45

Asn Lys Glu Asn Val Asp Thr Val Leu Asp Ile Gly Ser Gln Gly
        50                  55                  60

Ser Ile Glu Ala Leu Pro Ala Gln Ile Ser Lys Leu Thr Asp Gly Ile
 65                  70                  75                  80

Asp Ile Thr Leu Ile Asn Ala Gly Ile Ala Tyr Ser Met Tyr Ser Ile
                 85                  90                  95

Phe Glu Cys Ser Arg Glu Thr Phe Ile Asp His Trp Thr Thr Asn Ser
            100                 105                 110

Leu Gly Pro Ile Met Leu Tyr Lys Glu Ile His Gln Phe Met Leu Lys
        115                 120                 125

Arg Glu Thr Arg Lys Val Phe Phe Met Ser Ser Gly Gly Gly Ser Ile
    130                 135                 140

Gln Ser Leu Leu Pro Ile Ser Thr Ser Ala Tyr Gly Met Ser Lys Ala
145                 150                 155                 160

Ala Leu Asn Tyr Ala Val Arg Lys Leu Ser Asp Glu Cys Tyr Lys Asp
                165                 170                 175

Asn Phe Thr Ile Val Met Leu His Pro Gly Val Val Ala Thr Asp Met
```

-continued

```
                180                 185                 190
Gly Arg Glu Thr Thr Lys Ile Met Ala Asn Gly Asn Ala Gln Ile Ile
        195                 200                 205

Ser Tyr Ile Glu Ser Ile Ser Leu Pro Pro Ala Thr Ser Ala Ala Gln
    210                 215                 220

Thr Ile Gly Ala Met Gln Ala Leu Asp Lys Gln Ser Asn Gly Arg Phe
225                 230                 235                 240

Ile Gly Val Ala Asp Gln Phe Asp Ile Pro Phe
                245                 250

<210> SEQ ID NO 5
<211> LENGTH: 20
<212> TYPE: DNA
<213> ORGANISM: Artificial
<220> FEATURE:
<223> OTHER INFORMATION: Primer 1
<220> FEATURE:
<221> NAME/KEY: misc_feature
<222> LOCATION: (3)..(3)
<223> OTHER INFORMATION: n represents a, t, g or c
<220> FEATURE:
<221> NAME/KEY: misc_feature
<222> LOCATION: (6)..(6)
<223> OTHER INFORMATION: n represents a, t, g or c
<220> FEATURE:
<221> NAME/KEY: misc_feature
<222> LOCATION: (9)..(9)
<223> OTHER INFORMATION: y represents t or c
<220> FEATURE:
<221> NAME/KEY: misc_feature
<222> LOCATION: (12)..(12)
<223> OTHER INFORMATION: y represents t or c
<220> FEATURE:
<221> NAME/KEY: misc_feature
<222> LOCATION: (15)..(15)
<223> OTHER INFORMATION: h represents a, c, or t
<220> FEATURE:
<221> NAME/KEY: misc_feature
<222> LOCATION: (18)..(18)
<223> OTHER INFORMATION: n represents a, t, g or c

<400> SEQUENCE: 5
acngtntayt tyathgcngg                                           20

<210> SEQ ID NO 6
<211> LENGTH: 20
<212> TYPE: DNA
<213> ORGANISM: Artificial
<220> FEATURE:
<223> OTHER INFORMATION: Primer 2
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: d represents a or g or t
<220> FEATURE:
<221> NAME/KEY: misc_feature
<222> LOCATION: (9)..(9)
<223> OTHER INFORMATION: r represents g or a
<220> FEATURE:
<221> NAME/KEY: misc_feature
<222> LOCATION: (12)..(12)
<223> OTHER INFORMATION: r represents g or a
<220> FEATURE:
<221> NAME/KEY: misc_feature
<222> LOCATION: (15)..(15)
<223> OTHER INFORMATION: y represents t or c
<220> FEATURE:
<221> NAME/KEY: misc_feature
```

```
<222> LOCATION: (18)..(18)
<223> OTHER INFORMATION: r represents g or a

<400> SEQUENCE: 6
atnggdatrt craaytgrtc                                                 20

<210> SEQ ID NO 7
<211> LENGTH: 703
<212> TYPE: DNA
<213> ORGANISM: Ogataea minuta var. minuta

<400> SEQUENCE: 7
agcatcgaga gggattggcc tcgagattgc aacccaattg agtgcaaacc cagagaacca     60
tgtgattgcc tcgtacagat ctgaaaagac tgctggtgca ctcctggaac ttgccaagaa    120
ggacaacgtg acactgttg tgttggatat tgcaatccag gagtcgattg agggtttgtc    180
ccaacagatt gtgaagctga cggacggaat tgatattgct ctgatcaatg ccggagttgg    240
atactcaatg tactctctac tcgaatgttc cagagaagca ttcattgacc actggactac    300 aaattcctg ggtccaatcc tggtgtataa ggaaatccac caattcatgc tgaagagaga    360
aactcgaaaa gtgttcttca tgtctagcgg agcagggtct attcagggcc acttgcctgt    420
ttccgtgagt gcatacggta tgtcgaaggc agcactgaac tacgcggccc ggaaactttc    480
tgacgaatgc tacaaagacg gctttactat tgtggcgctt cacccaggta tggttctgac    540
agacatgggt atggagagta ttgagattat ggcaaacgga gacgagcagc ttgccgcgtc    600
catcaacagt attgcaatta gtacagacac tagtgccgca caatgcattg gtgcaatgca    660
gagtcttaca aagcagagca acggtagatt cattaatgtt gca                      703

<210> SEQ ID NO 8
<211> LENGTH: 703
<212> TYPE: DNA
<213> ORGANISM: Ogataea minuta var. minuta

<400> SEQUENCE: 8
agcttctaga ggtattggcc ttgaggttgc cactcagctg agtgccaacc cagataatta     60
tgttattggt tcttacagaa cggagaaaac tgcagctgag ctgctcaaac tggccaacaa    120
agaaaatgtc gacactgttg tcctagacat tggtagccaa ggttctattg aagcgcttcc    180
agcacaaatc tcaaagctga cggacggaat cgatattact ctgatcaatg ccggaattgc    240
gtactcaatg tactctatttt tcgagtgttc cagagagaca tttattgatc actgaccac    300 aaattccttg ggtccaatca tgctctacaa ggagattcat cagttcatgc tgaagagaga    360
aactcgtaag gtgtttttca tgtctagtgg aggaggctct atccagtctc tattgcctat    420
ttcaaccagt gcttacggta tgtcgaaggc tgcactgaac tatgcggtcc ggaagctttc    480
tgatgaatgc tacaaggaca acttcaccat tgtgatgttg cacccaggag tggtggccac    540
ggatatgggc cggaaaacta ccaagatcat ggccaatgga aatgctcaga ttatctctta    600
tattgaatcc atatctttgc cgcccgctac aagcgctgca cagactattg gtgcaatgca    660
agctcttgac aagcagagca atggtaggtt catcggagtc gca                      703

<210> SEQ ID NO 9
<211> LENGTH: 28
<212> TYPE: DNA
<213> ORGANISM: Artificial
<220> FEATURE:
<223> OTHER INFORMATION: Primer 3
```

```
<400> SEQUENCE: 9
gtgcatatga ccaagactgt ttatttca                                          28

<210> SEQ ID NO 10
<211> LENGTH: 30
<212> TYPE: DNA
<213> ORGANISM: Artificial
<220> FEATURE:
<223> OTHER INFORMATION: Primer 4

<400> SEQUENCE: 10
gtcgaattct tattaaaatg gaatgtcgaa                                        30

<210> SEQ ID NO 11
<211> LENGTH: 28
<212> TYPE: DNA
<213> ORGANISM: Artificial
<220> FEATURE:
<223> OTHER INFORMATION: Primer 5

<400> SEQUENCE: 11
gtgcatatgg ctaagactgt ctatttca                                          28

<210> SEQ ID NO 12
<211> LENGTH: 30
<212> TYPE: DNA
<213> ORGANISM: Artificial
<220> FEATURE:
<223> OTHER INFORMATION: Primer 6

<400> SEQUENCE: 12
gtcgaattct tactagaatg gaatgtcaaa                                        30

<210> SEQ ID NO 13
<211> LENGTH: 32
<212> TYPE: DNA
<213> ORGANISM: Artificial
<220> FEATURE:
<223> OTHER INFORMATION: Primer 7

<400> SEQUENCE: 13
gccgaattct aaggaggtta acaatgtata aa                                     32

<210> SEQ ID NO 14
<211> LENGTH: 28
<212> TYPE: DNA
<213> ORGANISM: Artificial
<220> FEATURE:
<223> OTHER INFORMATION: Primer 8

<400> SEQUENCE: 14
gcggtcgact tatccgcgtc ctgcttgg                                          28

<210> SEQ ID NO 15
<211> LENGTH: 756
<212> TYPE: DNA
<213> ORGANISM: Artificial
<220> FEATURE:
<223> OTHER INFORMATION: Mutant DNA 1

<400> SEQUENCE: 15
atgaccaaga ctgtttattt cattgccgga gcttctagag gtattggcct tgaggttgcc       60
actcagctga gtgccaaccc agataattat gttattggtt cttacagaac ggagaaaact      120
gcaggtgcgc tgctcgaact ggccaagaaa gaaaatgtcg acactgttgt cctagacatt      180
```

-continued

```
ggtagccaag gttctattga agcgcttcca gcacaaatct caaagctgac ggacggaatc    240
gatattactc tgatcaatgc cggaattgcg tactcaatgt actctatttt cgagtgttcc    300
agagagacat ttattgatca ctggaccaca aattccttgg gtccaatcat gctctacaag    360
gagattcatc agttcatgct gaagagagaa actcgtaagg tgttttttcat gtctagtgga   420 ggaggctcta tccagtctct attgcctatt tcaaccagtg cttacggtat gtcgaaggct    480
gcactgaact atgcggtccg gaagctttct gatgaatgct acaaggacaa cttcaccatt    540
gtgatgttgc acccaggagt ggtggccacg gatatgggcc gggaaactac caagatcatg    600
gccaatggaa atgctcagat tatctcttat attgaatcca tatctttgcc gcccgctaca    660
agcgctgcac agactattgg tgcaatgcaa gctcttgaca agcagagcaa tggtaggttc    720
atcggagtcg cagaccagtt cgacattcca ttttaa                              756
```

<210> SEQ ID NO 16
<211> LENGTH: 251
<212> TYPE: PRT
<213> ORGANISM: Artificial
<220> FEATURE:
<223> OTHER INFORMATION: Mutant polypeptide 1

<400> SEQUENCE: 16

```
Met Thr Lys Thr Val Tyr Phe Ile Ala Gly Ala Ser Arg Gly Ile Gly
1               5                   10                  15

Leu Glu Val Ala Thr Gln Leu Ser Ala Asn Pro Asp Asn Tyr Val Ile
            20                  25                  30

Gly Ser Tyr Arg Thr Glu Lys Thr Ala Gly Ala Leu Leu Glu Leu Ala
        35                  40                  45

Lys Lys Glu Asn Val Asp Thr Val Val Leu Asp Ile Gly Ser Gln Gly
    50                  55                  60

Ser Ile Glu Ala Leu Pro Ala Gln Ile Ser Lys Leu Thr Asp Gly Ile
65                  70                  75                  80

Asp Ile Thr Leu Ile Asn Ala Gly Ile Ala Tyr Ser Met Tyr Ser Ile
                85                  90                  95

Phe Glu Cys Ser Arg Glu Thr Phe Ile Asp His Trp Thr Thr Asn Ser
            100                 105                 110

Leu Gly Pro Ile Met Leu Tyr Lys Glu Ile His Gln Phe Met Leu Lys
        115                 120                 125

Arg Glu Thr Arg Lys Val Phe Phe Met Ser Ser Gly Gly Gly Ser Ile
    130                 135                 140

Gln Ser Leu Leu Pro Ile Ser Thr Ser Ala Tyr Gly Met Ser Lys Ala
145                 150                 155                 160

Ala Leu Asn Tyr Ala Val Arg Lys Leu Ser Asp Glu Cys Tyr Lys Asp
                165                 170                 175

Asn Phe Thr Ile Val Met Leu His Pro Gly Val Val Ala Thr Asp Met
            180                 185                 190

Gly Arg Glu Thr Thr Lys Ile Met Ala Asn Gly Asn Ala Gln Ile Ile
        195                 200                 205

Ser Tyr Ile Glu Ser Ile Ser Leu Pro Pro Ala Thr Ser Ala Ala Gln
    210                 215                 220

Thr Ile Gly Ala Met Gln Ala Leu Asp Lys Gln Ser Asn Gly Arg Phe
225                 230                 235                 240

Ile Gly Val Ala Asp Gln Phe Asp Ile Pro Phe
                245                 250
```

CARBONYL REDUCTASE, GENE THEREOF AND METHOD OF USING THE SAME

TECHNICAL FIELD

The present invention relates to a polypeptide (carbonyl-reductase) having an activity to asymmetrically reduce (3S)-1-chloro-3-tert-butoxycarbonylamino-4-phenyl-2-butanone represented by the following formula (1):

(1)

to produce (2R,3S)-1-chloro-3-tert-butoxycarbonylamino-4-phenyl-2-butanol represented by the following formula (2):

(2)

, which is isolated from a microorganism having the activity, a DNA encoding the polypeptide, a vector containing the DNA, and a transformant transformed with the vector.

The present invention also relates to a production method of an optically active alcohol, particularly (2R,3S)-1-chloro-3-tert-butoxycarbonylamino-4-phenyl-2-butanol represented by the aforementioned formula (2), using the polypeptide or the transformant.

(2R,3S)-1-Chloro-3-tert-butoxycarbonylamino-4-phenyl-2-butanol is a compound useful as a synthetic starting material for a pharmaceutical agent and the like.

BACKGROUND ART

As the production method of (2R,3S)-1-chloro-3-tert-butoxycarbonylamino-4-phenyl-2-butanol, a method comprising chemically reducing amino-protected (3S)-1-halo-3-amino-4-phenyl-2-butanone derivative with a reducing agent such as sodium borohydride and the like is known (patent reference 1, non-patent reference 1). However, this method requires a comparatively expensive reducing agent, and the stereoselectivity thereof is not practically sufficient.

As a method using a microorganism, moreover, a method comprising allowing a microorganism belonging to the genus *Candida* and the like to act on a (3S)-1-halo-3-amino-4-phenyl-2-butanone derivative to produce a (2R,3S)-1-halo-3-amino-4-phenyl-2-butanol derivative (patent reference 2), and a method comprising bringing a microorganism belonging to the genus *Rhodococcus* and the like in contact with (3S)-1-halo-2-oxo-3-protected amino-4-substituted butane to produce (2R,3S)-1-halo-2-hydroxy-3-protected amino-4-substituted butane (patent reference 3, non-patent reference 2) are known. By these methods, however, the concentration of the product that can be accumulated in the reaction mixture cannot be practically sufficient.

patent reference 1: JP-A-2-42048
patent reference 2: JP-A-9-285
patent reference 3: WO2002/014528
non-patent reference 1: Tetrahedron, 50, 6333 (1994)
non-patent reference 2: Tetrahedron: Asymmetry, 14, 3105 (2003)

DISCLOSURE OF THE INVENTION

Problems to be Solved by the Invention

In view of the above, the present invention aims at providing a polypeptide useful for the production of (2R,3S)-1-chloro-3-tert-butoxycarbonylamino-4-phenyl-2-butanol, a DNA encoding the polypeptide, a vector containing the DNA, and a transformant transformed with the vector.

In addition, the present invention aims at providing an efficient production method of various optically active alcohols including (2R,3S)-1-chloro-3-tert-butoxycarbonylamino-4-phenyl-2-butanol, using the polypeptide or the transformant.

Means of Solving the Problems

The present inventors have isolated a polypeptide having an activity to asymmetrically reduce (3S)-1-chloro-3-tert-butoxycarbonylamino-4-phenyl-2-butanone to produce (2R,3S)-1-chloro-3-tert-butoxycarbonylamino-4-phenyl-2-butanol from a microorganism having the activity. Moreover, they have succeeded in clarifying the base sequence of a DNA encoding the polypeptide and generating a transformant that highly produces the polypeptide utilizing the sequence. In addition, they have found that various useful optically active alcohols such as (2R,3S)-1-chloro-3-tert-butoxycarbonylamino-4-phenyl-2-butanol can be efficiently produced by utilizing the polypeptide or the transformant, which resulted in the completion of the present invention.

That is, the present invention is directed to a polypeptide having an activity to asymmetrically reduce (3S)-1-chloro-3-tert-butoxycarbonylamino-4-phenyl-2-butanone to produce (2R,3S)-1-chloro-3-tert-butoxycarbonylamino-4-phenyl-2-butanol.

Moreover, the present invention provides a DNA encoding the polypeptide. Furthermore, the present invention provides a vector containing the DNA. In addition, the present invention provides a transformant containing the vector. Further, the present invention provides a production method of optically active alcohols including (2R,3S)-1-chloro-3-tert-butoxycarbonylamino-4-phenyl-2-butanol, using the polypeptide or the transformant.

EFFECT OF THE INVENTION

According to the present invention, a practical production method of useful optically active alcohols including (2R,3S)-1-chloro-3-tert-butoxycarbonylamino-4-phenyl-2-butanol can be provided.

BEST MODE FOR EMBODYING THE INVENTION

The present invention is explained in detail in the following.

(3S)-1-Chloro-3-tert-butoxycarbonylamino-4-phenyl-2-butanone described in the present specification can be prepared, for example, by the method disclosed in JP-A-62-126158 or JP-A-2-42048. In addition, unless otherwise specified, isolation of DNA, preparation of vector, gene manipulation such as transformation described in the present specification can be performed by methods described in books such as Molecular Cloning 2nd Edition (Cold Spring Harbor Laboratory Press, 1989) and the like. Moreover, "%" used in the description of the present specification means "% (w/v)" unless otherwise specified.

The polypeptide of the present invention is a polypeptide having an activity to asymmetrically reduce (3S)-1-chloro-3-tert-butoxycarbonylamino-4-phenyl-2-butanone to produce (2R,3S)-1-chloro-3-tert-butoxycarbonylamino-4-phenyl-2-butanol. Such polypeptide can be isolated from a microorganism having the activity.

While the microorganism to be the origin of the polypeptide of the present invention is not particularly limited, for example, a yeast belonging to the genus *Ogataea* can be used. Particularly preferred is *Ogataea minuta* var. *minuta*, NBRC0975 strain. The microorganism can be obtained from the Incorporated Administrative Agency, National Institute of Technology and Evaluation, Biological Resource Center (NBRC: 2-5-8 Kazusakamatari, Kisarazu-shi 292-0818 Chiba, Japan).

As a medium for cultivating a microorganism to be the origin of the polypeptide of the present invention, general liquid nutritional media including carbon sources, nitrogen sources, inorganic salts, organic nutrients and the like can be used as long as the microorganism grows.

The polypeptide of the present invention can be isolated from the microorganism to be the origin of the polypeptide by appropriately combining generally known protein purification methods. For example, the isolation can be performed as follows.

First, the microorganism is cultured in a suitable medium, and the cells are collected from the cultured medium by centrifugation or filtration. The obtained cells were disrupted by a physical means using an ultrasonic disintegrator, glass beads and the like, and the cellular debris was removed by centrifugation to give a cell-free extract. Then, the polypeptide of the present invention is isolated from the cell-free extract by a method such as salting-out (ammonium sulfate precipitation, sodium phosphate precipitation and the like), solvent precipitation (protein fractionation precipitation by acetone, ethanol and the like), dialysis, gel filtration chromatography, ion exchange chromatography, reversed-phase chromatography, ultrafiltration and the like, alone or in combination.

The activity to reduce (3S)-1-chloro-3-tert-butoxycarbonylamino-4-phenyl-2-butanone can be determined, for example, by adding a 0.2 mM substrate, (3S)-1-chloro-3-tert-butoxycarbonylamino-4-phenyl-2-butanone, a 0.25 mM coenzyme, NADPH and a crude enzyme to a 100 mM phosphate buffer (pH 6.5) containing 0.33% (v/v) dimethyl sulfoxide, reacting the mixture at 30° C. for 1 min and calculating the activity from the decreasing rate of absorbance at a wavelength of 340 nm after the reaction.

In addition, the determination of absolute configuration and measurement of diastereomeric excess of (3S)-1-chloro-3-tert-butoxycarbonylamino-4-phenyl-2-butanol produced by the above-mentioned reaction can be performed by high performance liquid chromatography (column: COSMOSIL 5C8-MS (φ4.6 mm×250 mm; manufactured by Nacalai Tesque), eluent: 10 mM aqueous phosphoric acid solution/acetonitrile=1/1 (v/v), flow rate: 1 ml/min, detection: 210 nm).

The DNA of the present invention is a DNA encoding the aforementioned polypeptide of the present invention, and may be any as long as it can express the polypeptide in a host cell transformed according to the below-mentioned method, and may contain any untranslated region. Once the polypeptide can be acquired, those of ordinary skill in the art can obtain such DNA by a known method from a microorganism to be the origin of the polypeptide. For example, it can be obtained by the following method.

First, an isolated polypeptide of the present invention is digested with a suitable endopeptidase, and the resulting peptide fragments are fractionated by reversed-phase HPLC. Then, for example, using an ABI492 protein sequencer (manufactured by Applied Biosystems), a part or the whole amino acid sequence of the peptide fragments are determined.

Based on the information of the amino acid sequence obtained in this way, PCR (Polymerase Chain Reaction) primers for amplifying a part of a DNA encoding the polypeptide are synthesized. Then, a chromosomal DNA of a microorganism to be the origin of the polypeptide is prepared by a general DNA isolation method, for example, the method of Visser and the like (Appl. Microbiol. Biotechnol., 53, 415 (2000)). Using the chromosomal DNA as a template and the aforementioned PCR primers, PCR is performed to amplify a part of the DNA encoding the polypeptide and determine the base sequence thereof. The base sequence can be determined, for example, using ABI373A DNA Sequencer (manufactured by Applied Biosystems) and the like.

Once a part of the base sequence of the DNA encoding the polypeptide is clarified, the full-length sequence can be determined, for example, by i-PCR (Nucl. Acids Res., 16, 8186 (1988)).

Examples of the DNA of the present invention obtained in this way include a DNA containing the base sequence shown in SEQ ID NO: 1 and a DNA containing the base sequence shown in SEQ ID NO: 2. In addition, a DNA that hybridizes to a DNA consisting of a base sequence complementary to the base sequence shown in SEQ ID NO: 1 or SEQ ID NO: 2 under stringent conditions, which encodes a polypeptide having an activity to asymmetrically reduce (3S)-1-chloro-3-tert-butoxycarbonylamino-4-phenyl-2-butanone to produce (2R,3S)-1-chloro-3-tert-butoxycarbonylamino-4-phenyl-2-butanol, is also encompassed in the DNA of the present invention.

The DNA that hybridizes to a DNA consisting of a base sequence complementary to the base sequence shown in SEQ ID NO: 1 or SEQ ID NO: 2 under stringent conditions refers to a DNA that specifically forms a hybrid with a DNA having a base sequence complementary to the base sequence shown in SEQ ID NO: 1 or SEQ ID NO: 2, when colony hybridization method, plaque hybridization method, Southern hybridization method and the like are performed.

As used herein the stringent conditions refer to, for example, the conditions under which hybridization in an aqueous solution of a composition of 75 mM trisodium citrate, 750 mM sodium chloride, 0.5% sodium dodecylsulfate, 0.1% bovine serum albumin, 0.1% polyvinylpyrrolidone and 0.1% Ficoll 400 (manufactured by Amersham Biosciences) is performed at 65° C., followed by washing with an aqueous solution of a composition of 15 mM trisodium citrate, 150 mM sodium chloride, and 0.1% sodium dodecylsulfate at 60°

C. Preferably, they refer to the conditions under which washing with an aqueous solution of a composition of 15 mM trisodium citrate, 150 mM sodium chloride, and 0.1% sodium dodecylsulfate is performed at 65° C. after hybridization under the above-mentioned conditions. More preferably, they refer to the conditions under which washing with an aqueous solution of a composition of 1.5 mM trisodium citrate, 15 mM sodium chloride, and 0.1% sodium dodecylsulfate is performed at 65° C. after the hybridization in the same manner as above.

Examples of the polypeptide of the present invention include a polypeptide having the amino acid sequence shown in SEQ ID NO: 3 encoded by the base sequence shown in SEQ ID NO: 1 and a polypeptide having the amino acid sequence shown in SEQ ID NO: 4 encoded by the base sequence shown in SEQ ID NO: 2.

In addition, a polypeptide showing at least a certain level of homology to either of these two kinds of polypeptides and having an activity to asymmetrically reduce (3S)-1-chloro-3-tert-butoxycarbonylamino-4-phenyl-2-butanone to produce (2R,3S)-1-chloro-3-tert-butoxycarbonylamino-4-phenyl-2-butanol is functionally equivalent to these two kinds of polypeptides and encompassed in the present invention.

As used herein, the homology of the sequence is expressed, for example, by the value of Identity relative to the whole sequence when two amino acid sequences are comparatively analyzed using a homology search program FASTA (W. R. Pearson & D. J. Lipman; Pro. Natl. Acad. Sci. USA, 85, 2444-2448 (1988)). Examples of the polypeptide equivalent to the polypeptide shown in SEQ ID NO: 3 or SEQ ID NO: 4 include a polypeptide showing not less than 78% (a homology between the polypeptide shown in SEQ ID NO: 3 and the polypeptide shown in SEQ ID NO: 4 is 78%), preferably not less than 80%, more preferably not less than 85%, still more preferably not less than 90%, of homology to either of these two kinds of polypeptides.

Such polypeptide can be obtained, for example, by ligating a DNA that can be hybridized to a DNA consisting of a base sequence complementary to the base sequence shown by the aforementioned SEQ ID NO: 1 or SEQ ID NO: 2 under stringent conditions, into a suitable vector and introducing the vector into a suitable host cell to allow expression. Moreover, such polypeptide can be obtained, for example, by causing substitution, insertion, deletion or addition of amino acid in a polypeptide having the amino acid sequence shown in SEQ ID NO: 3 or SEQ ID NO: 4, according to a known method described in Current Protocols in Molecular Biology (John Wiley and Sons, Inc., 1989) and the like.

Examples of the polypeptide obtained by the latter method include a polypeptide obtained by substituting the 42nd alanine with glycine, the 43rd glutamic acid with alanine, the 46th lysine with glutamic acid and/or the 49th asparagine with lysine in the amino acid sequence shown in SEQ ID NO: 4. A polypeptide having all these four mutations (mutant polypeptide 1) is shown in SEQ ID NO: 16, and a DNA encoding the polypeptide (mutant DNA 1) is shown in SEQ ID NO: 15.

The vector to be used for introducing the DNA of the present invention into a host microorganism to allow expression of the DNA in the host microorganism is not particularly limited as long as the DNA can express the encoded gene in a suitable host microorganism. Examples of the vectors include plasmid vector, phage vector, cosmid vector and the like. In addition, a shuttle vector capable of gene exchange with other host cells can also be used.

Such vector generally contains a regulator such as lacUV5 promoter, trp promoter, trc promoter, tac promoter, lpp promoter, tufB promoter, recA promoter, pL promoter and the like, and can be preferably used as an expression vector containing an expression unit operably linked to the DNA of the present invention. For example, pUCNT (WO94/03613) can be preferably used.

The term "regulator" used in the present specification refers to a base sequence having a functional promoter and any related transcriptional element (e.g., enhancer, CCAAT box, TATA box, SPI moiety and the like).

The term "operably linked" used in the present specification means that various regulatory elements such as a promoter, an enhancer and the like, that control the gene expression, and a gene are connected in an operable state in a host cell. It is a well known matter to those of ordinary skill in the art that the type and kind of regulator can vary depending on the host.

Examples of the expression vector of the present invention include pNTOM3 wherein the DNA shown in SEQ ID NO: 1 has been introduced into PUCNT, pNTOM4 wherein the DNA shown in SEQ ID NO: 2 has been introduced into pUCNT, pNTOM5 wherein the DNA shown in SEQ ID NO: 15 has been introduced into pUCNT, which are mentioned below, and the like.

As the host cell, into which a vector containing the DNA of the present invention is introduced, bacterium, yeast, filamentous bacterium, plant cell, animal cell and the like can be used. Since introduction and/or culture are/is easy, bacterium is preferable, and *Escherichia coli* is particularly preferable. The vector containing the DNA of the present invention can be introduced into a host cell by a known method. When *Escherichia coli* is used as a host cell, for example, a commercially available *E. coli* HB101 competent cell (manufactured by TAKARA BIO) can be used to introduce the vector into the host cell.

Examples of the transformant of the present invention include *E. coli* HB101 (pNTMO3) FERM BP-10368 wherein the aforementioned pNTMO3 has been introduced into *E. coli* HB101, *E. coli* HB101 (pNTOM4) FERM BP-10369 wherein the aforementioned pNTMO4 has been introduced into *E. coli* HB101, *E. coli* HB101 (pNTOM5) FERM BP-10370 wherein the aforementioned pNTMO5 has been introduced into *E. coli* HB101, which are mentioned below, and the like. These transformants have been respectively deposited under the aforementioned accession numbers in the National Institute of Advanced Industrial Science and Technology, International Patent Organism Depositary (IPOD: Central 6, 1-1-1, Higashi, Tsukuba, Ibaraki, 305-8566 Japan) (date of original deposit in Japan on Jun. 3, 2004, the national deposit strains were transferred to the international deposit based on Budapest Treaty on Jul. 6, 2005).

When a compound having a carbonyl group is asymmetrically reduced to produce an optically active alcohol using the polypeptide of the present invention, a coenzyme such as NADH, NADPH and the like becomes necessary. However, the amount of an expensive coenzyme to be used can be drastically reduced by carrying out the reaction in the co-presence of a polypeptide capable of converting the oxidized coenzyme to a reduced form (hereinafter to be referred to as a coenzyme regenerating capability) a compound to be a substrate of the polypeptide, and the polypeptide of the present invention.

As the polypeptide having the coenzyme regenerating capability, for example, hydrogenase, formic acid dehydrogenase, alcohol dehydrogenase, aldehyde dehydrogenase, glucose-6-phosphate dehydrogenase, glucose dehydrogenase and the like can be used. Preferably, glucose dehydrogenase is used.

The optically active alcohol can be produced using the polypeptide of the present invention as follows. First, a compound having a carbonyl group to be the substrate, a coenzyme such as NADPH and the like, and the polypeptide are added to a suitable solvent, and the mixture is stirred under an adjusted pH to carry out the reaction. When the reaction is carried out using the polypeptide of the present invention and a polypeptide having a coenzyme regenerating capability in combination, a polypeptide having a coenzyme regenerating capability (e.g., glucose dehydrogenase) and a compound (e.g., glucose) to be its substrate are further added to the above-mentioned reaction composition.

An aqueous solvent may be used for the reaction or a mixture of an aqueous solvent and an organic solvent may be used for the reaction. Examples of the organic solvent include toluene, ethyl acetate, n-butyl acetate, hexane, isopropanol, diisopropyl ether, methanol, acetone, dimethyl sulfoxide and the like. The reaction is carried out at a temperature of 10° C.-70° C., and the pH of the reaction mixture is maintained at 4-10. The reaction can be carried out by a batch process or a continuous process. For a batch process, the reaction substrate is added at a charge concentration of from 0.1% to 70% (w/v). Examples of the compound having a carbonyl group to be a substrate include (3S)-1-chloro-3-tert-butoxycarbonylamino-4-phenyl-2-butanone. However, the compound is not particularly limited as long as it can be reduced under the aforementioned reaction conditions and converted to an optically active alcohol.

The reaction can be carried out similarly even when a transformant containing a DNA encoding the polypeptide, or a treated product thereof is used instead of the polypeptide of the present invention. Moreover, the reaction can be carried out similarly even when a transformant containing both a DNA encoding the polypeptide of the present invention and a DNA encoding a polypeptide having a coenzyme regenerating capability, or a treated product thereof is used. The "treated product of transformant" means, for example, a cell treated with a surfactant or an organic solvent, a dried cell, a disrupted cell, crude extract of a cell and the like, as well as those fixed by a known means.

Particularly, when a transformant containing both a DNA encoding the polypeptide of the present invention and a DNA encoding a polypeptide having a coenzyme regenerating capability or a treated product thereof is used, an enzyme for regenerating a coenzyme does not need to be separately prepared and added, and an optically active alcohol can be produced efficiently.

A transformant containing both a DNA encoding the polypeptide of the present invention and a DNA encoding a polypeptide having a coenzyme regenerating capability can be obtained by incorporating both the DNA encoding the polypeptide of the present invention and the DNA encoding a polypeptide having a coenzyme regenerating capability into a single vector, and introducing the vector into a host cell, or respectively incorporating these two kinds of DNAs into two kinds of vectors belonging to different incompatible groups, and introducing the two kinds of vectors into a single host cell.

Examples of the vector incorporating both a DNA encoding the polypeptide of the present invention and a DNA encoding a polypeptide having a coenzyme regenerating capability include pNTOM3G1, pNTOM4G1 and pNTOM5G1, wherein a glucose dehydrogenase gene derived from *Bacillus megaterium* has been introduced into each of the aforementioned expression vectors pNTOM3, pNTOM4 and pNTOM5, and the like. Examples of the transformant containing both the DNA encoding the polypeptide of the present invention and the DNA encoding a polypeptide having a coenzyme regenerating capability include *E. coli* HB101 (pNTOM3G1), *E. coli* HB101 (pNTOM4G1) and *E. coli* HB101 (pNTOM5G1), wherein *E. coli* HB101 has been transformed with these vectors, and the like.

The activity of a polypeptide having a coenzyme regenerating capability in a transformant can be determined by a conventional method. For example, the activity of glucose dehydrogenase can be calculated from the rate of increase in the absorbance at a wavelength of 340 nm, when 100 mM glucose, 2 mM coenzyme NADP or NAD, and the enzyme are added to 1M Tris-HCl buffer (pH 8.0), and the mixture is reacted at 25° C. for 1 min.

A transformant containing a DNA encoding the polypeptide of the present invention can be cultured in a conventional liquid nutritional medium containing carbon sources, nitrogen sources, inorganic salts, organic nutrients and the like, as long as it grows.

An optically active alcohol resulting from a reaction can be purified by a conventional method. For example, when the optically active alcohol resulting from a reaction is (2R,3S)-1-chloro-3-tert-butoxycarbonylamino-4-phenyl-2-butanol, the reaction mixture is extracted with an organic solvent such as ethyl acetate, toluene and the like, and the organic solvent is evaporated under reduced pressure. Moreover, it can be purified by a treatment such as crystal precipitation, chromatography and the like.

For quantitation of (3S)-1-chloro-3-tert-butoxycarbonylamino-4-phenyl-2-butanone and (2R,3S)-1-chloro-3-tert-butoxycarbonylamino-4-phenyl-2-butanol, as well as for measurement of diastereomeric excess of (2R,3S)-1-chloro-3-tert-butoxycarbonylamino-4-phenyl-2-butanol, high performance liquid chromatography (column: COSMOSIL 5C8-MS ($\phi$ 4.6 mm×250 mm; manufactured by Nacalai Tesque), eluent: 10 mM aqueous phosphoric acid solution/acetonitrile=1/1, flow rate: 1 ml/min, detection: 210 nm) can be used.

As mentioned above, according to the present invention, the polypeptide of the present invention can be efficiently produced and, utilizing the polypeptide, a superior production method of various useful optically active alcohols including (2R,3S)-1-chloro-3-tert-butoxycarbonylamino-4-phenyl-2-butanol can be provided.

EXAMPLES

The present invention is explained in detail in the following Examples, which are not to be construed as limitative. The detailed operation method and the like relating to the recombinant DNA technique used in the following Examples is described in the following books: Molecular Cloning 2nd Edition (Cold Spring Harbor Laboratory Press, 1989), Current Protocols in Molecular Biology (Greene Publishing Associates and Wiley-Interscience).

Example 1

Purification of Polypeptide

According to the following method, a polypeptide having an activity to asymmetrically reduce (3S)-1-chloro-3-tert-butoxycarbonylamino-4-phenyl-2-butanone to produce (2R, 3S)-1-chloro-3-tert-butoxycarbonylamino-4-phenyl-2-butanol was isolated and purified from the *Ogataea minuta* var. *minuta* NBRC0975 strain. Unless otherwise specified, the purification was performed at 4° C.

The reduction activity on (3S)-1-chloro-3-tert-butoxycarbonylamino-4-phenyl-2-butanone was determined by dissolving, in 100 mM phosphate buffer (pH 6.5) containing 0.33% (v/v) dimethyl sulfoxide, a substrate [(3S)-1-chloro-3-tert-butoxycarbonylamino-4-phenyl-2-butanone] to a final concentration of 0.2 mM and a coenzyme NADPH to a final concentration of 0.25 mM, further adding a crude enzyme solution, carrying out the reaction at 30° C. for 1 min and calculating from the rate of decrease in the absorbance of the reaction mixture at a wavelength of 340 nm. The activity to oxidize 1 μmol of NADPH to NADP for 1 min under said reaction conditions was defined to be 1 unit.

(Culture of Microorganism)

A liquid medium (18 L) (pH 6.5) containing glucose 5%, polypeptone 0.5%, yeast extract 0.1%, dipotassium hydrogen phosphate 0.1%, potassium dihydrogen phosphate 0.2% and magnesium sulfate heptahydrate 0.02%, was prepared in a 30 L jar-fermentor (manufactured by B.E. Marubishi Co., Ltd.) and sterilized with vapor at 120° C. for 20 min.

To this medium was inoculated 180 ml of a cultured medium of the *Ogataea minuta* var. *minuta* NBRC0975 strain precultured in the same medium in advance, and the mixture was cultured under the conditions of stirring at 250 rpm, airflow amount 5.0 NL/min, 28° C. for 48 hr.

(Preparation of Cell-Free Extract)

The cells were collected from the above-mentioned cultured medium by centrifugation and washed with 2000 ml of 10 mM Tris-HCl buffer (pH 7.5) to give 907 g of the cells of the strain. The cells were suspended in 1800 ml of 10 mM Tris-HCl buffer (pH 7.5) containing 0.1 mM dithiothreitol (DTT), and disrupted using a UH-600 ultrasonication dispersion machine (manufactured by SMT). The cell debris was removed from the disrupt by centrifugation to give a cell-free extract.

(Ammonium Sulfate Fractionation)

The pH of the cell-free extract obtained above was adjusted to 7.5 with aqueous ammonia, ammonium sulfate was added and dissolved to 40% saturation while maintaining the pH, and the resulting precipitate was removed by centrifugation. Ammonium sulfate was further added to the supernatant and dissolved to 60% saturation while maintaining at pH 7.5 in the same manner as above, and the resulting precipitate was collected by centrifugation. The precipitate was dissolved in 10 mM Tris-HCl buffer (pH 7.5) containing 0.1 mM DTT, and dialyzed against the same buffer overnight to give an active fraction.

(DEAE-Sephacel Column Chromatography)

The active fraction obtained by ammonium sulfate fractionation was applied to a DEAE-Sephacel (manufactured by Amersham Biosciences) column (ϕ29×290 mm) equilibrated in advance with 10 mM Tris-HCl buffer (pH 7.5) containing 0.1 mM DTT to allow adsorption of the active fraction. After washing the column with the same buffer, the active fraction was eluted with the linear gradient (from 0 M to 1 M) of sodium chloride. The active fraction was collected and dialyzed against the same buffer overnight.

(MonoQ HR Column Chromatography)

The active fraction obtained by DEAE-Sephacel column chromatography was applied to a MonoQ HR 10/10 column (manufactured by Amersham Biosciences) equilibrated in advance with 10 mM Tris-HCl buffer (pH 7.5) containing 0.1 mM DTT to allow adsorption of the active fraction. After washing the column with the same buffer, the active fraction was eluted with the linear gradient (from 0 M to 1 M) of sodium chloride. The active fraction was collected and dialyzed against the same buffer overnight.

(Phenyl-Superose Column Chromatography)

Sodium chloride was dissolved in the active fraction obtained by MonoQ HR column chromatography to a final concentration of 4M and the solution was applied to a Phenyl-Superose HR 10/10 column (manufactured by Amersham Biosciences) equilibrated in advance with 10 mM Tris-HCl buffer (pH 7.5) containing 4 M sodium chloride and 0.1 mM DTT to allow adsorption of the active fraction. After washing the column with the same buffer, the active fraction was eluted with the linear gradient (from 4 M to 0 M) of sodium chloride. The active fraction was collected and dialyzed against 10 mM Tris-HCl buffer (pH 7.5) containing 0.1 mM DTT overnight.

(MonoQ HR Column Chromatography)

The active fraction obtained by Phenyl-Superose column chromatography was applied to a MonoQ HR 5/5 column (manufactured by Amersham Biosciences) equilibrated in advance with 10 mM Tris-HCl buffer (pH 7.5) containing 0.1 mM DTT to allow adsorption of the active fraction. After washing the column with the same buffer, the active fraction was eluted with the linear gradient (from 0 M to 1 M) of sodium chloride. The active fraction was collected and concentrated using Centricon YM-10 (manufactured by Millipore).

(Gel Filtration Chromatography)

The active fraction obtained by the aforementioned MonoQ HR column chromatography was applied to a Superdex 200 HR 10/30 column (manufactured by Amersham Biosciences) equilibrated in advance with 10 mM Tris-HCl buffer (pH 7.5) containing 0.2 M sodium chloride and 0.1 mM DTT and the active fraction was eluted at a flow rate of 0.5 ml/min using the same buffer. The active fraction was collected and concentrated using Centricon YM-10 (manufactured by Millipore). This was applied to a Superdex 200 HR 10/30 column (manufactured by Amersham Biosciences) equilibrated in advance with the same buffer and the active fraction was eluted at a flow rate of 0.5 ml/min using the same buffer. The active fraction was collected and used as a purified standard sample of the polypeptide.

Example 2

Gene Cloning (Preparation of PCR Primers)

The purified polypeptide obtained in Example 1 was denatured in the presence of 8M urea and digested with lysyl endopeptidase derived from Achromobacter (manufactured by Wako Pure Chemical Industries, Ltd.). Then, the amino acid sequence of the obtained peptide fragment was determined by ABI492 protein sequencer (manufactured by Perkin Elmer). Based on the DNA sequence predicted from the amino acid sequence, primer 1: 5'-acngtntayttyathgcngg-3' (SEQ ID NO: 5) and primer 2: 5'-atnggdatrtcraaytgrtc-3' (SEQ ID NO: 6) for amplifying a part of the gene encoding the polypeptide by PCR were synthesized.

(Gene Amplification by PCR)

Chromosomal DNA was extracted from the cells of *Ogataea minuta* var. *minuta* NBRC0975 strain cultured in the same manner as in Example 1 according to the method of Visser (Appl. Microbiol. Biotechnol., 53, 415 (2000)) and the like. Using the DNA primers 1 and 2 prepared above and the obtained chromosomal DNA as a template, PCR was performed. As a result, about 700 bp DNA fragment considered to be a part of the object gene was amplified. PCR was performed using TaKaRa Ex Taq (manufactured by TAKARA BIO) as a DNA polymerase, where the reaction conditions followed the instruction manual thereof. The DNA fragment was cloned to a plasmid pT7Blue T-Vector (manufactured by Novagen), and the base sequence thereof was analyzed using ABI PRISM Dye Terminator Cycle Sequencing Ready Reaction Kit (manufactured by Perkin Elmer) and ABI 373A DNA Sequencer (manufactured by Perkin Elmer). As a result of the PCR, it has been clarified that two kinds of DNA fragments having different base sequences were amplified. The base sequences thereof are shown in SEQ ID NO: 7 and SEQ ID NO: 8.

(Identification of Full-Length Sequence of Object Gene by i-PCR)

The chromosomal DNA of *Ogataea minuta* var. *minuta* NBRC0975 strain prepared above was completely digested with a restriction enzyme XbaI, a mixture of the obtained DNA fragments was intramolecularly cyclized with T4 ligase. Using this as a template, the full-length base sequence of the gene containing the aforementioned base sequence shown in SEQ ID NO: 7 was determined by i-PCR (Nucl. Acids Res., 16, 8186 (1988)). The results are shown in SEQ ID NO: 1. i-PCR was performed using TaKaRa LA Taq (manufactured by TAKARA BIO) as a DNA polymerase, where the reaction conditions followed the instruction manual thereof. The full-length base sequence of the gene containing the aforementioned base sequence shown in SEQ ID NO: 8 was also determined by a similar operation, and the results thereof are shown in SEQ ID NO: 2. In addition, the amino acid sequence encoded by the base sequence shown in SEQ ID NO: 1 is shown in SEQ ID NO: 3, and the amino acid sequence encoded by the base sequence shown in SEQ ID NO: 2 is shown in SEQ ID NO: 4.

Example 3

Construction of Expression Vector

Using primer 3: 5'-gtgcatatgaccaagactgtttatttca-3' (SEQ ID NO: 9) and primer 4: 5'-gtcgaattcttattaaaatggaatgtcgaa-3' (SEQ ID NO: 10) and the chromosomal DNA of the *Ogataea minuta* var. *minuta* NBRC0975 strain obtained in Example 2 as a template, PCR was performed. As a result, a double stranded DNA wherein an NdeI recognition site is added to the initiation codon and an EcoRI recognition site is added immediately after the termination codon of a gene having the base sequence shown in SEQ ID NO: 2 was obtained. PCR was performed using TaKaRa LA Taq (manufactured by TAKARA BIO) as a DNA polymerase, where the reaction conditions followed the instruction manual thereof. The DNA was digested with NdeI and EcoRI, and inserted between the NdeI recognition site and the EcoRI recognition site in the downstream of the lac promoter of plasmid pUCNT (WO94/03613) to construct a recombinant vector pNTOM4.

Similarly, using primer 5: 5'-gtgcatatggctaagactgtctatttca-3' (SEQ ID NO: 11) and primer 6: 5'-gtcgaattcttactagaatg-gaatgtcaaa-3'(SEQ ID NO: 12), a double stranded DNA wherein an NdeI recognition site is added to the initiation codon and an EcoRI recognition site is added immediately after the termination codon of a gene having the base sequence shown in SEQ ID NO: 1 was obtained. The DNA was inserted into plasmid pUCNT in the same manner as above to construct a recombinant vector pNTOM3.

Example 4

Preparation of Mutant Gene

Using Mutan-SuperExpress Km (manufactured by TAKARA BIO) and following the operation method described in the instruction manual thereof, a mutant gene wherein, in the gene having the base sequence shown in SEQ ID NO: 2, the 125th C was substituted by G, the 128th A was substituted by C, the 136th A was substituted by G, and the 147th C was substituted by G, was prepared. The mutant gene encodes a polypeptide wherein, in the amino acid sequence shown in SEQ ID NO: 4, the 42nd alanine is substituted by glycine, the 43rd glutamic acid is substituted by alanine, the 46th lysine is substituted by glutamic acid, and the 49th asparagine is substituted by lysine. The base sequence of the mutant gene is shown in SEQ ID NO: 15, and the amino acid sequence of the mutant polypeptide encoded by the gene is shown in SEQ ID NO: 16. The mutant gene was inserted into a vector pUCNT in the same manner as in Example 3 to construct a recombinant vector pNTOM5.

Example 5

Construction of Expression Vector Further Containing Glucose Dehydrogenase Gene

Using primer 7: 5'-gccgaattctaaggaggttaacaatgtataaa-3' (SEQ ID NO: 13) and primer 8: 5'-gcggtcgacttatccgcgtcct-gcttgg 3' (SEQ ID NO: 14) and plasmid pGDK1 (Eur. J. Biochem., 186, 389 (1989)) as a template, PCR was performed to give a double stranded DNA wherein, in a glucose dehydrogenase (hereinafter to be referred to as GDH) gene derived from *Bacillus megaterium* IAM1030 strain, an *Escherichia coli* ribosome binding sequence is added at 5 bases upstream of the initiation codon, an EcoRI cleavage point is added immediately before the ribosome binding sequence and a SalI cleavage point is added immediately after the stop codon, was obtained.

Figure 1:
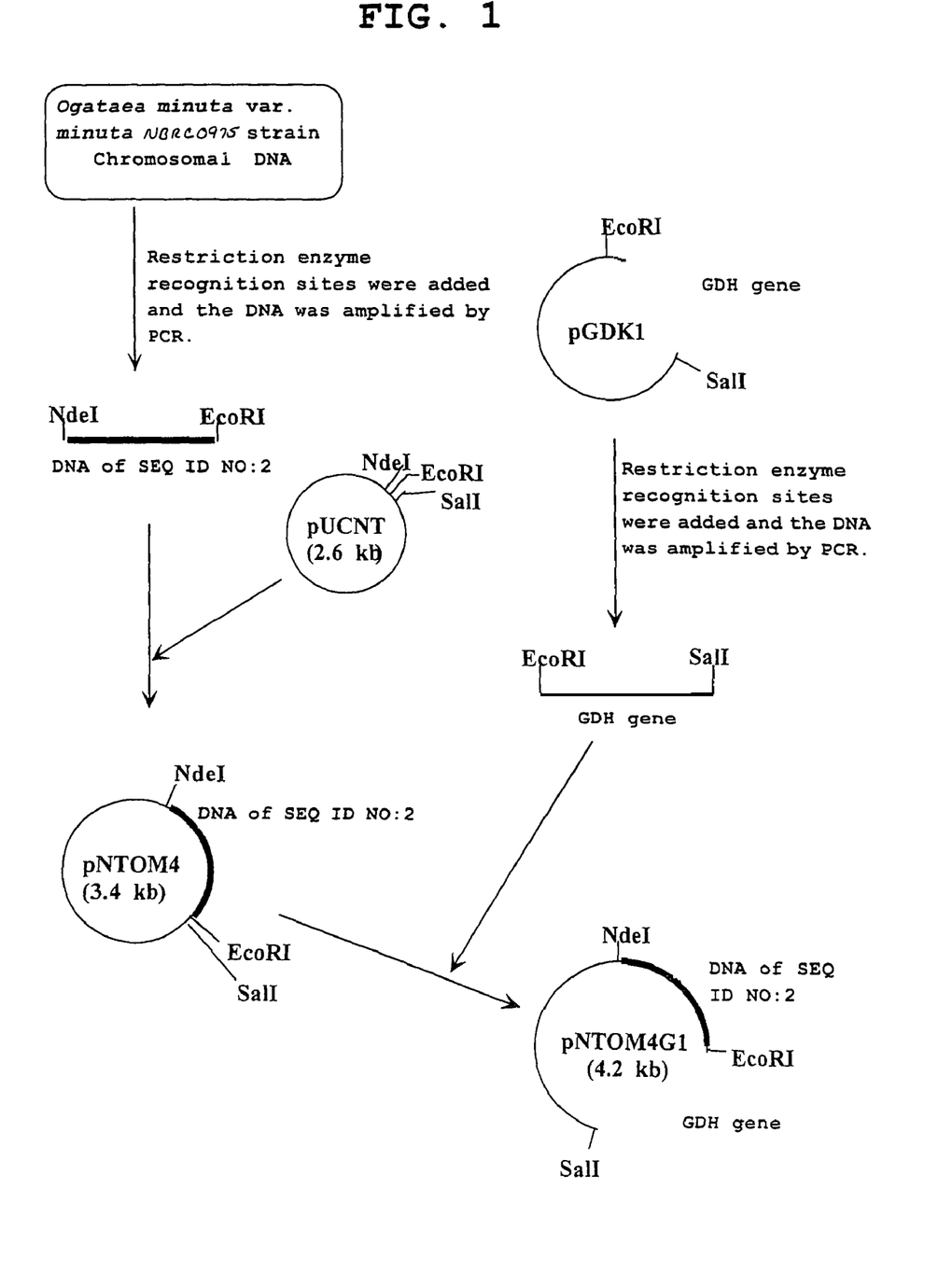
FIG. 1 shows a production method and a structure of a recombinant vector pNTOM4G1.

The obtained DNA fragment was digested with EcoRI and SalI, and inserted into the EcoRI and SalI sites of pNTOM3, pNTOM4 and pNTOM5 constructed in Examples 3 and 4 to construct recombinant plasmids pNTOM3G1, pNTOM4G1 and pNTOM5G1. As an example, the production method and structure of pNTOM4G1 are shown in FIG. 1.

Example 6

Preparation of Transformant

Using the recombinant vectors pNTOM3, pNTOM4 and pNTOM5 constructed in Examples 3 and 4, *E. coli* HB101 competent cell (manufactured by TAKARA BIO) was transformed to give *E. coli* HB101 (pNTOM3), *E. coli* HB101 (pNTOM4) and *E. coli* HB101 (pNTOM5). These transformants have been deposited under accession numbers FERM BP-10368, FERM BP-10369 and FERM BP-10370, respectively, in the National Institute of Advanced Industrial Science and Technology, International Patent Organism Depositary (IPOD).

Similarly, using the recombinant vectors pNTOM3G1, pNTOM4G1 and pNTOM5G1 constructed in Example 5, *E. coli* HB101 competent cell (manufactured by TAKARA BIO)

was transformed to give *E. coli* HB101 (pNTOM3G1), *E. coli* HB101 (pNTOM4G1) and *E. coli* HB101 (pNTOM5G1).

Example 7

Gene Expression in Transformant

Six kinds of transformants obtained in Example 6 and *E. coli* HB101 (pUCNT), which is a transformant containing a vector plasmid pUCNT, were inoculated to 50 ml of 2×YT medium (tryptone 1.6%, yeast extract 1.0%, NaCl 0.5%, pH 7.0) containing 200 µg/ml ampicillin, and cultured with shaking at 37° C. for 24 hr. The cells were collected by centrifugation, and suspended in 50 ml of 100 mM phosphate buffer (pH 6.5). The cells were disrupted with a UH-50 ultrasonication homogenizer (manufactured by SMT), and cell debris was removed by centrifugation to give a cell-free extract. The (3S)-1-chloro-3-tert-butoxycarbonylamino-4-phenyl-2-butanone reduction activity and GDH activity of the cell-free extract were measured and expressed as the specific activity in Table 1. In all of the 6 kinds of transformants obtained in Example 6, expression of the (3S)-1-chloro-3-tert-butoxycarbonylamino-4-phenyl-2-butanone reduction activity was observed. In *E. coli* HB101 (pNTOM3G1), *E. coli* HB101 (pNTOM4G1) and *E. coli* HB101 (pNTOM5G1), containing a GDH gene, expression of the GDH activity was also observed. The (3S)-1-chloro-3-tert-butoxycarbonylamino-4-phenyl-2-butanone reduction activity was measured by the method described in Example 1. The GDH activity was calculated from rate of increase in the absorbance at a wavelength of 340 nm, when 0.1 M glucose, 2 mM coenzyme NADP, and a crude enzyme solution were added to 1M Tris-HCl buffer (pH 8.0), and the mixture was reacted at 25° C. for 1 min. The enzyme activity to reduce 1 µmol of NADP to NADPH for 1 min under said reaction conditions was defined to be 1 unit. In addition, the protein concentration in the cell-free extract was measured using a protein assay kit (manufactured by BIO-RAD).

TABLE 1

| strain | CBPB* reduction activity (U/mg) | GDH activity (U/mg) |
| --- | --- | --- |
| *E. coli* HB101 (pUCNT) | 0.0 | 0 |
| *E. coli* HB101 (pNTOM3) | 6.3 | 0 |
| *E. coli* HB101 (pNTOM4) | 5.0 | 0 |
| *E. coli* HB101 (pNTOM5) | 14.0 | 0 |
| *E. coli* HB101 (pNTOM3G1) | 5.7 | 119 |
| *E. coli* HB101 (pNTOM4G1) | 3.5 | 157 |
| *E. coli* HB101 (pNTOM5G1) | 9.0 | 122 |

CBPB*: (3S)-1-chloro-3-tert-butoxycarbonylamino-4-phenyl-2-butanone

Example 8

Reaction Using Transformant

Glucose dehydrogenase (manufactured by Amano Enzyme) 2000 U, glucose 2 g, NADP 6 mg, (3S)-1-chloro-3-tert-butoxycarbonylamino-4-phenyl-2-butanone 2.5 g were added to 50 ml of a cell-free extract of *E. coli* HB101 (pNTOM3) prepared in Example 7, and the mixture was stirred at 30° C. for 22 hr while adjusting to pH 6.5 by dropwise addition of 5 M sodium hydroxide. After completion of the reaction, the reaction mixture was extracted with toluene, desolvated and the extract was analyzed. As a result, (2R,3S)-1-chloro-3-tert-butoxycarbonylamino-4-phenyl-2-butanol (yield 86.3%, diastereomeric excess 96.4% d.e.) was obtained.

For quantitation of (3S)-1-chloro-3-tert-butoxycarbonylamino-4-phenyl-2-butanone and (3S)-1-chloro-3-tert-butoxycarbonylamino-4-phenyl-2-butanol, as well as for measurement of diastereomeric excess of (2R,3S)-1-chloro-3-tert-butoxycarbonylamino-4-phenyl-2-butanol, high performance liquid chromatography (column: COSMOSIL 5C8-MS (φ 4.6 mm×250 mm; manufactured by Nacalai Tesque), eluent: 10 mM aqueous phosphoric acid solution/acetonitrile=1/1, flow rate: 1 ml/min, detection: 210 nm) was used.

Example 9

Reaction Using Transformant

Glucose dehydrogenase (manufactured by Amano Enzyme) 1250 U, glucose 3 g, NADP 4 mg, (3S)-1-chloro-3-tert-butoxycarbonylamino-4-phenyl-2-butanone 0.25 g were added to 22.5 ml of a cell-free extract of *E. coli* HB101 (pNTOM4) prepared in Example 7, and the mixture was stirred at 30° C. while adjusting to pH 6.5 by dropwise addition of 5 M sodium hydroxide. (3S)-1-chloro-3-tert-butoxycarbonylamino-4-phenyl-2-butanone (0.25 g) was added at 2 hr, 4 hr and 6 hr from the start of the reaction and 1.25 g thereof was added at 8 hr from the start of the reaction, and the mixture was reacted for 31 hr. After completion of the reaction, the reaction mixture was extracted with toluene, desolvated and the extract was analyzed in the same manner as in Example 8. As a result, (2R,3S)-1-chloro-3-tert-butoxycarbonylamino-4-phenyl-2-butanol (yield 99.0%, diastereomeric excess 99.8% d.e.) was obtained.

Example 10

Reaction Using Transformant

Glucose 3 g, NADP 3 mg, toluene 0.25 ml, and (3S)-1-chloro-3-tert-butoxycarbonylamino-4-phenyl-2-butanone 2.5 g were added to 25 ml of a cultured medium of *E. coli* HB101 (pNTOM4G1) prepared in the same manner as in Example 7, and the mixture was stirred at 30° C. for 40 hr while adjusting to pH 6.5 by dropwise addition of 5 M sodium hydroxide. After completion of the reaction, the reaction mixture was extracted with toluene, desolvated and the extract was analyzed in the same manner as in Example 8. As a result, (2R,3S)-1-chloro-3-tert-butoxycarbonylamino-4-phenyl-2-butanol (yield 99.1%, diastereomeric excess 99.8% d.e.) was obtained.

Example 11

Reaction Using Transformant

Glucose 6 g, NADP 1.4 mg, toluene 0.25 ml, and (3S)-1-chloro-3-tert-butoxycarbonylamino-4-phenyl-2-butanone 2.5 g were added to 50 ml of a cultured medium of *E. coli* HB101 (pNTOM5G1) prepared in the same manner as in Example 7, and the mixture was stirred at 30° C. while adjusting to pH 6.5 by dropwise addition of 5 M sodium hydroxide.

One hour after the start of the reaction, 2.5 g of (3S)-1-chloro-3-tert-butoxycarbonylamino-4-phenyl-2-butanone was added, and the mixture was reacted for 20 hr. After completion of the reaction, the reaction mixture was extracted with toluene, desolvated and the extract was analyzed in the same manner as in Example 8. As a result, (2R,3S)-1-chloro-3-tert-butoxycarbonylamino-4-phenyl-2-butanol (yield 99.6%, diastereomeric excess 99.8% d.e.) was obtained.

Example 12

Substrate Specificity of Polypeptide

In 100 mM phosphate buffer (pH 6.5) containing 0.33% (v/v) dimethyl sulfoxide were dissolved a carbonyl compound to be a substrate to a final concentration of 1 mM, and a coenzyme NADPH to a final concentration of 0.25 mM, respectively. Thereto was added a cell-free extract of *E. coli* HB101 (pNTOM4) or *E. coli* HB101 (pNTOM3) prepared in Example 7, and the mixture was reacted at 30° C. for 1 min. The reduction activity on each carbonyl compound was calculated from the rate of decrease in the absorbance of the reaction mixture at a wavelength of 340 nm, and shown in Table 2 as a value relative to the activity on (3S)-1-chloro-3-tert-butoxycarbonylamino-4-phenyl-2-butanone as 100%. The polypeptides consisting of the amino acid sequences shown in SEQ ID NO: 3 and SEQ ID NO: 4, which were produced by the transformants, both showed reduction activity on a wide range of carbonyl compounds.

TABLE 2

Substrate specificity of polypeptides produced by transformant

| substrate (carbonyl compound) | relative activity (%) E. coli HB101 | |
|---|---|---|
| | (pNTOM3) | (pNTOM4) |
| CBPB* | 100 | 100 |
| 2-acetylpyridine | 29 | 0 |
| 3-acetylpyridine | 15 | 0 |
| 4-acetylpyridine | 98 | 0 |
| acetylpyrazine | 185 | 0 |
| acetophenone | 215 | 0 |
| 3'-hydroxyacetophenone | 33 | 0 |
| 3'-nitroacetophenone | 273 | 31 |
| 4'-chloroacetophenone | 35 | 9 |
| 4'-fluoroacetophenone | 28 | 1 |
| 3',4'-dimethoxyacetophenone | 51 | 4 |
| 4'-methylacetophenone | 41 | 1 |
| 2-hydroxyacetophenone | 32 | 1 |
| 2-chloro-1-(3'-chlorophenyl)ethanone | 1301 | 33 |
| 1-phenyl-2-butanone | 285 | 2 |
| propiophenone | 183 | 2 |
| benzoin | 4018 | 5 |

TABLE 2-continued

Substrate specificity of polypeptides produced by transformant

| substrate (carbonyl compound) | relative activity (%) E. coli HB101 | |
|---|---|---|
| | (pNTOM3) | (pNTOM4) |
| benzylacetone | 66 | 0 |
| ethyl benzoylformate | 296 | 20 |
| ethyl 2-oxo-4-phenylbutyrate | 127 | 106 |
| acetone | 47 | 0 |
| 2-butanone | 22 | 0 |
| 2-hexanone | 11 | 0 |
| 2-heptanone | 102 | 0 |
| 2-octanone | 808 | 3 |
| chloroacetone | 100 | 1 |
| hydroxyacetone | 51 | 0 |
| diacetyl | 444 | 5 |
| acetylacetone | 23 | 0 |
| cyclopentanone | 8 | 0 |
| 7-methoxy-2-tetoralone | 599 | 6 |
| 1-tetoralone | 146 | 1 |
| ethyl 3-oxocyclopentanecarboxylate | 484 | 12 |
| methyl pyruvate | 674 | 5 |
| ethyl pyruvate | 1067 | 23 |
| methyl acetoacetate | 8 | 0 |
| ethyl acetoacetate | 137 | 0 |
| tert-butyl acetoacetate | 1330 | 2 |
| ethyl 2-methylacetoacetate | 619 | 4 |
| ethyl 2-chloroacetoacetate | 3309 | 40 |
| ethyl 2-eteneacetoacetate | 2013 | 10 |
| ethyl 2-oxodecanoate | 985 | 5 |
| ethyl 4-chloroacetoacetate | 4547 | 22 |
| n-octyl 4-chloroacetoacetate | 466 | 24 |
| ethyl 4-bromoacetoacetate | 476 | 7 |
| ethyl 4-azideacetoacetate | 659 | 1 |
| ethyl 4-benzyloxyacetoacetate | 1259 | 8 |
| ethyl 4-acetoxyacetoacetate | 465 | 1 |
| benzyl acetoacetate | 883 | 4 |
| ethyl benzoylacetate | 1233 | 0 |
| ethyl 2-chloro-3-oxo-3-phenylpropionate | 716 | 5 |
| benzaldehyde | 81 | 1 |
| 2-pyridinecarbaldehyde | 56 | 1 |
| pyridine-4-aldehyde | 571 | 2 |
| o-chlorobenzaldehyde | 269 | 17 |
| m-chlorobenzaldehyde | 344 | 17 |
| p-chlorobenzaldehyde | 91 | 12 |
| o-nitrobenzaldehyde | 1621 | 89 |
| m-nitrobenzaldehyde | 851 | 29 |
| p-nitrobenzaldehyde | 1166 | 21 |
| propionaldehyde | 99 | 0 |
| n-butylaldehyde | 168 | 0 |
| n-hexylaldehyde | 265 | 3 |
| 2-phenylpropionaldehyde | 479 | 3 |
| 3-phenylpropionaldehyde | 2410 | 7 |
| glutaraldehyde | 80 | 1 |

CBPB*: (3S)-1-chloro-3-tert-butoxycarbonylamino-4-phenyl-2-butanone

The invention claimed is:

1. An isolated DNA comprising the base sequence of SEQ ID NO: 2.

2. An isolated DNA encoding a polypeptide selected from the group consisting of:
   (a) a polypeptide comprising the amino acid sequence of SEQ ID NO: 4, and
   (b) a polypeptide having the amino acid sequence of SEQ ID NO: 4 except for at least one modification in SEQ ID NO: 4 selected from the group consisting of:
      (1) the alanine at position 42 of SEQ ID NO: 4 is substituted by glycine,
      (2) the glutamic acid at position 43 of SEQ ID NO: 4 is substituted by alanine,
      (3) the lysine at position 46 of SEQ ID NO: 4 is substituted by glutamic acid, and
      (4) the asparagine at position 49 of SEQ ID NO: 4 is substituted by lysine.

3. A vector comprising the DNA of claim 1.

4. The vector of claim 3, further comprising a DNA encoding a polypeptide having a glucose dehydrogenase activity.

5. The vector of claim 4, wherein the polypeptide having a glucose dehydrogenase activity is a glucose dehydrogenase derived from *Bacillus megaterium*.

6. An isolated host cell transformed with the vector of claim 3.

7. The isolated host cell of claim 6, which is *Escherichia coli*.

8. The isolated host cell of claim 7 which is *E. coli* HB101 (pNTOM4) FERM BP-10369.

9. A vector comprising the DNA of claim 2.

10. The vector of claim 9, further comprising a DNA encoding a polypeptide having a glucose dehydrogenase activity.

11. The vector of claim 10, wherein the polypeptide having a glucose dehydrogenase activity is a glucose dehydrogenase derived from *Bacillus megaterium*.

12. An isolated host cell transformed with the vector of claim 9.

13. The isolated host cell of claim 12, which is *Escherichia coli*.

14. A method of producing an optically active alcohol, which comprises reacting the isolated host cell of claim 6 or a treated product thereof, with a compound having a carbonyl group,
   wherein the treated product is selected from the group consisting of a cell treated with a surfactant or an organic solvent, a dried cell, a disrupted cell, crude extract of the cell, and a fixed cell, and
   wherein the carbonyl group is (3S)-1-chloro-3-tert-butoxycarbonylamino-4-phenyl-2-butanone, and the optically active alcohol is (2R, 3S)-1-chloro-3-tert-butoxycarbonylamino-4-phenyl-2-butanol.

15. A method of producing an optically active alcohol, which comprises reacting the isolated host cell of claim 12 or a treated product thereof, with a compound having a carbonyl group,
   wherein the treated product is selected from the group consisting of a cell treated with a surfactant or an organic solvent, a dried cell, a disrupted cell, crude extract of the cell, and a fixed cell, and
   wherein the carbonyl group is (3S)-1-chloro-3-tert-butoxycarbonylamino-4-phenyl-2-butanone, and the optically active alcohol is (2R, 3S)-1-chloro-3-tert-butoxycarbonylamino-4-phenyl-2-butanol.

* * * * *

UNITED STATES PATENT AND TRADEMARK OFFICE
CERTIFICATE OF CORRECTION

PATENT NO. : 7,794,993 B2
APPLICATION NO. : 11/659481
DATED : September 14, 2010
INVENTOR(S) : Noriyuki Kizaki et al.

Page 1 of 1

It is certified that error appears in the above-identified patent and that said Letters Patent is hereby corrected as shown below:

Title Page
In item (86) (PCT No.: PCT/JP2005/014006 371(c)(1),(2),(4) Date), on the face of the patent, Delete "Feb. 6, 2007"
Insert --Apr. 5, 2007--

Signed and Sealed this
Nineteenth Day of April, 2011

David J. Kappos
*Director of the United States Patent and Trademark Office*